(12) United States Patent
Kelly et al.

(10) Patent No.: US 6,462,247 B1
(45) Date of Patent: Oct. 8, 2002

(54) TOLUENE DISPROPORTIONATION PROCESS

(75) Inventors: Kevin Peter Kelly, Friendswood; James Roy Butler, Houston, both of TX (US)

(73) Assignee: Fina Technology, Inc., Dallas, TX (US)

( * ) Notice: Subject to any disclaimer, the term of this patent is extended or adjusted under 35 U.S.C. 154(b) by 707 days.

(21) Appl. No.: 08/679,889

(22) Filed: Jul. 15, 1996

(51) Int. Cl.⁷ .................................................. C07C 5/12
(52) U.S. Cl. ........................................ 585/475; 585/470
(58) Field of Search ................................. 585/470, 475

(56) References Cited

U.S. PATENT DOCUMENTS 3,629,351 A * 12/1971 Olive et al. .................. 585/475
3,677,973 A * 7/1972 Mitsche et al. ......... 252/455 Z \* cited by examiner

*Primary Examiner*—Thuan D. Dang

(57) ABSTRACT

A toluene disproportionation process is disclosed which converts toluene to benzene and xylenes over a nickel mordenite catalyst utilizing increased throughputs.

7 Claims, 15 Drawing Sheets

Test Using UOP Catalyst
Temperature and Conversion Rx 21

RX22 Plant UCI Selectivity

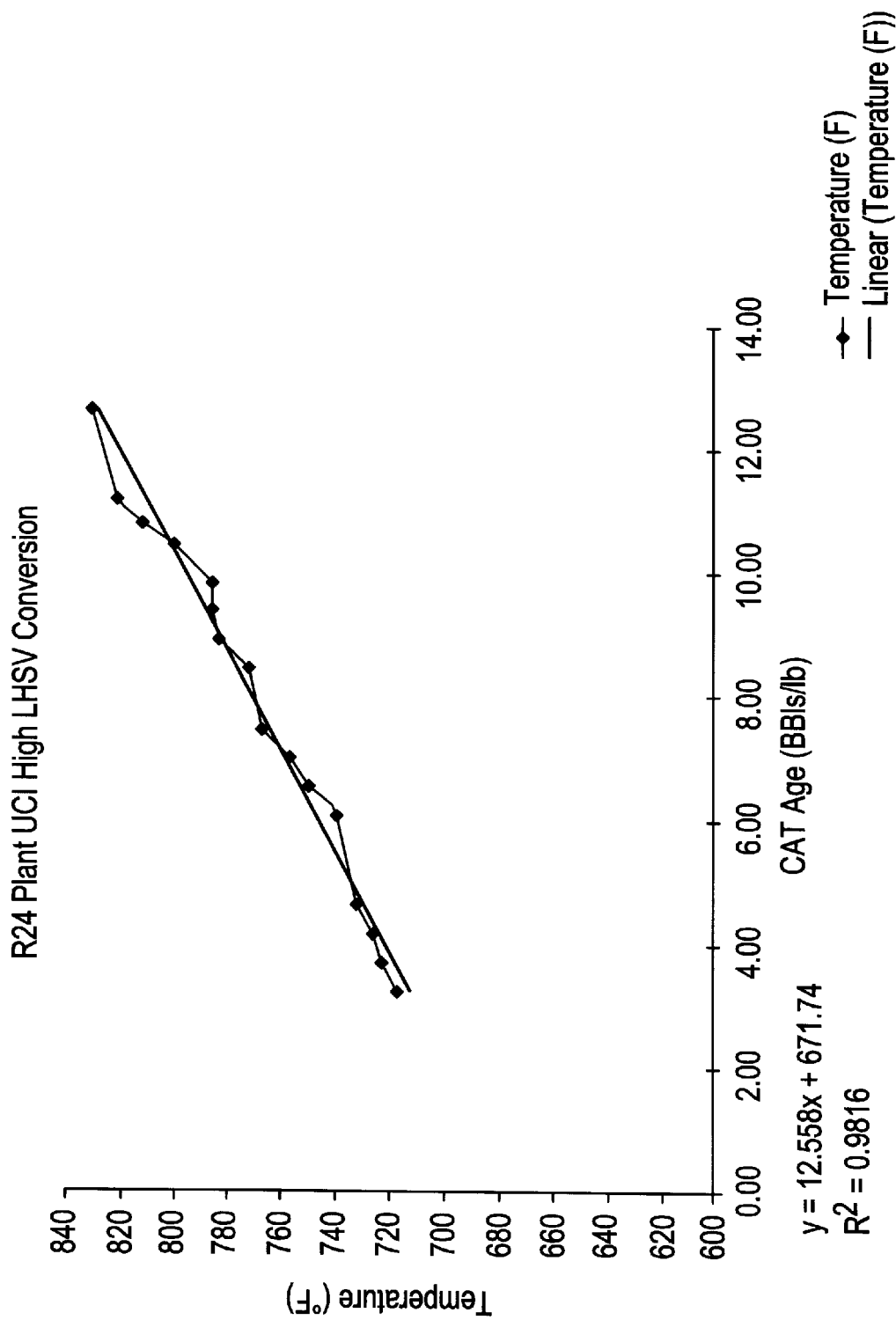

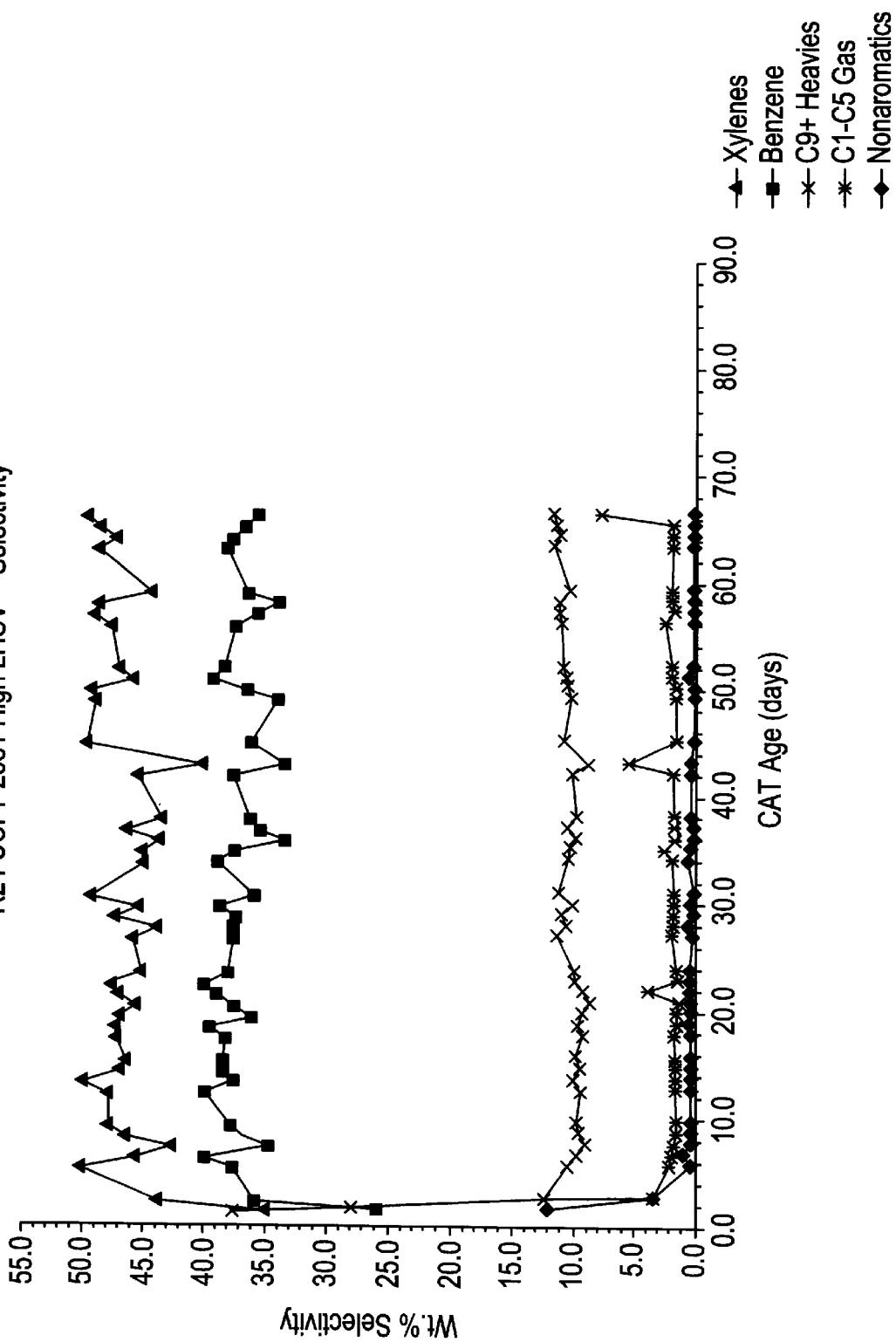

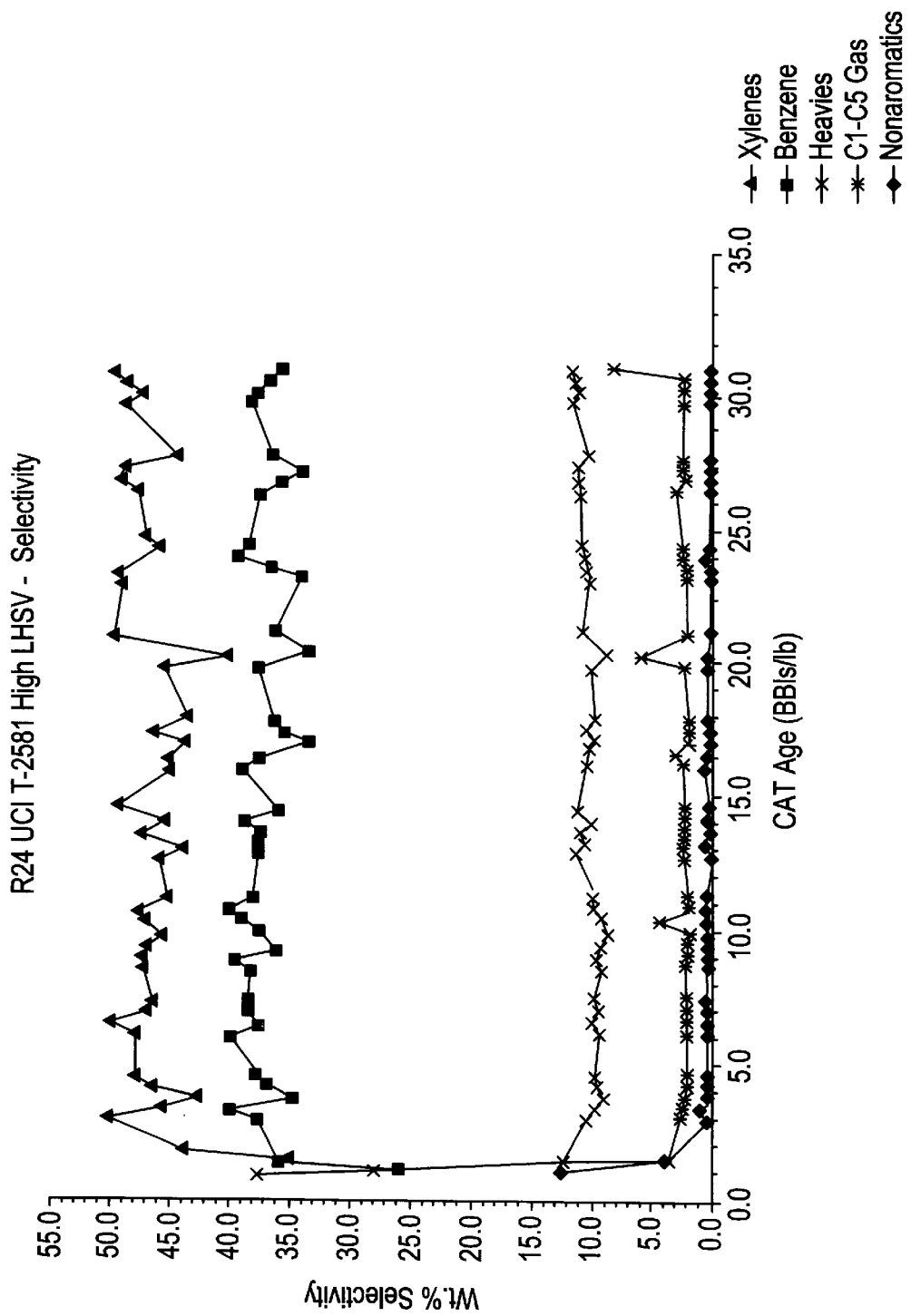

TOLUENE DISPROPORTIONATION PROCESS

BACKGROUND OF THE INVENTION

This invention relates to the disproportionation of alkylaromatic feedstreams and more particularly to disproportionation of toluene containing feedstocks employing dealuminated nickel mordenite catalysts.

DESCRIPTION OF THE RELATED ART

Toluene disproportionation (TDP) involves a well known transalkylation reaction in which toluene is converted to benzene and xylene in accordance with the following reaction:

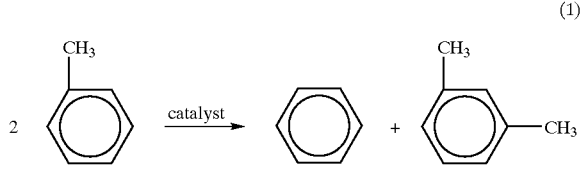

Mordenite is one of a number of molecular sieve catalysts useful in the transalkylation of alkylaromatic compounds. Mordenite is a crystalline aluminosilicate zeolite exhibiting a network of silicon and aluminum atoms interlinked by oxygen atoms within the crystalline structure. For a general description of mordenite catalysts, reference is made to Kirk-Othmer, Encyclopedia of Chemical Technology, 3rd Edition, 1981, under the heading "Molecular Sieves", Vol. 15, pages 638–643. Mordenite as found in nature or as synthesized to replicate the naturally occurring zeolite, typically exhibits a relatively low silica-to-alumina mole ratio of about 10 or less. Also known, however, are mordenite catalysts exhibiting a substantially lower alumina content. These alumina deficient mordenite catalysts exhibit silica-to-alumina ratios greater than 10, ranging up to about 100, and may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al. Both the typical and the aluminum deficient mordenites are known to be useful in the disproportionation of toluene.

Disproportionation of toluene feedstock may be performed at temperatures ranging from about 200° C. to about 600° C. or above and at pressures ranging from atmospheric to perhaps 100 atmospheres or above and at liquid hourly space velocities (LHSV) of around 2 hr$^{-2}$. The specific catalyst, however, may impose constraints on reaction temperatures in terms of catalyst activity and aging characteristics. In general, the prior art suggests the use of relatively high temperatures when employing the high aluminum mordenites (low silica-to-alumina ratios) and somewhat lower temperatures when employing the low alumina mordenites. Accordingly, where mordenite catalysts exhibiting high silica/alumina ratios have been employed in the transalkylation of alkylaromatics, it has been the practice to operate toward the lower end of the temperature range. U.S. Pat. No. 4,665,258 to Butler et al., however, discloses disproportionation of a toluene containing feedstock employing an aluminum deficient mordenite catalyst under relatively severe disproportionation conditions; involving a temperature range of 370°–500° C. The mordenite catalysts exhibit silica/alumina mole ratios of at least 30 and, more desirably, within the range of 40–60. The feedstock may be supplied to the reaction zone containing the mordenite catalyst at rates providing relatively high space velocities. The toluene weight hourly space velocity (WHSV) may be greater than 1. Hydrogen is supplied to the reaction zone at a hydrogen/toluene mole ratio within the range of 3–6. The hydrogen pressure may be 500 psi or more. The toluene feedstock need not be dried before supplying it to the reaction zone and the patent discloses toluene feedstocks exhibiting a water content in excess of 100 ppm.

The Butler '258 patent also discloses passing a hot preflush gas, nitrogen or hydrogen, to the reaction zone prior to initiating the disproportionation reaction. The preflush gas is heated to a temperature sufficient to substantially dehydrate the catalyst by the time the toluene feed is started. This measure enables the disproportionation process to initially be performed at a somewhat lower temperature and without reduction in toluene conversion. As the disproportionation proceeds, temperature progressively increases to maintain toluene conversion at the desired level, typically about 80 percent of theoretical.

U. S. Pat. No. 4,723,049 to Menard et al. discloses toluene disproportionation carried out over aluminum deficient mordenite of the type disclosed in the aforementioned patent to Butler. In this process, preferably carried out at a reaction zone temperature of 370°–500° C., and more preferably at a temperature of 400°–500° C. with an unmodified aluminum deficient mordenite catalyst, the supply of toluene to the reaction zone is interrupted while the supply of hydrogen is continued. Preferably the period of interruption during which hydrogen supply is continued is for at least one day prior to reinstating the supply of toluene feedstock to the reaction zone. This mode of operation is disclosed to enhance the aging quality of the catalyst and show a reduction in reaction zone temperature without a corresponding decrease in toluene conversion.

It is also a common practice to promote an aluminum deficient mordenite catalyst with a catalytically active metallic content. For example, U.S. Pat. No. 3,476,821 to Brandenburg et al. discloses disproportionation reactions employing mordenite catalysts having silica/alumina ratios within the range of 10–100 and preferably within the range of 20–60. The mordenites are modified by the inclusion of a sulfided metal selected from the Group VIII metals. The metal may be included in the mordenite by well known ion exchange or impregnated techniques. The especially preferred sulfided Group VIII metals are cobalt and nickel present in a concentration of 0.5–10 weight percent. When compared with nickel oxide, nickel sulfide is said to provide less overactivity as indicated by gas and saturated hydrocarbon yield. Here the desired temperature ranges are said to be from about 400°–750° F. and preferably 450°–640° F. The metal promoters are said to substantially increase activity and catalyst life, as indicated by runs extending over several hours or days.

As noted previously, hydrogen is supplied along with toluene to the reaction zone. While the disproportionation reaction (1) does not involve chemical consumption of hydrogen, the use of a hydrogen cofeed is generally considered to prolong the useful life of the catalyst, as disclosed, for example, in the above mentioned patent to Brandenburg. The amount of hydrogen supplied, which is normally measured in terms of the hydrogen/toluene mole ratio, is generally shown in the prior art to increase as temperature increases.

Bhavikatti et al., "Toluene Disproportionation Over Aluminum-Deficient and Metal-Loaded Mordenites. 1.

Catalytic Activity and Aging", Ind. Eng. Chem. Prod. Res. Dev. 1981, 20, 102–105, discloses toluene disproportionation at 400° C. over mordenite catalysts having silica/alumina mole ratios ranging from 12 to 61 at atmospheric pressure and a space velocity (WHSV) of 1. As the silica/alumina mole ratio is increased, catalyst activity is substantially decreased while aging quality is increased. That is, the aging rates were lower. Based upon short term aging studies, the best silica/alumina mole ratio appeared to be 23. Catalyst decay was also suppressed by loading the mordenites with nickel. Mordenites having a silica/alumina ratio of 12, 16 and 23 were modified by the inclusion of nickel by a procedure involving ion exchanging ammonium mordenite with an aqueous solution of nickel nitrate. After ion exchange, the catalyst was activated under a hydrogen environment for two hours. The best activation temperature for nickel modified mordenite having a silica/alumina ratio of 23 was indicated to be about 550° C. The nickel modified mordenite having a silica/alumina ratio of 12 showed significantly lower activity when compared to the nickel loaded mordenite of a silica/alumina ratio of 23.

Other patents directed to toluene disproportionation catalysts and processes include Mitsche U.S. Pat. No. 3,562,345; Mitsche U.S. Pat. No. 3,677,973; Marcilly U.S. Pat. No. 4,151,120; Dufresne et al. U.S. Pat. No. 4,723,048; and Pollitzer U.S. Pat. No. 3,780,122.

A pre-reaction start-up procedure comprising passing a hot, inert gas (hydrogen or nitrogen) across the catalyst and reactor bed prior to feedstock introduction is disclosed in Butler et al., U.S. Pat. No. 4,956,511 and U.S. Pat. No. 4,665,258 also to Butler et al. Another pre-reaction, start-up procedure aimed at controlling the hygroscopic tendency of mordenite involves subjecting the catalyst to a dry calcination procedure as disclosed in U.S. Pat. No. 4,151,120 to Marcilly. All of the aforementioned U.S. patents and literature references are incorporated herein by reference.

Conventional TDP processes utilizing Ni-Mordenite catalysts suffer from numerous disadvantages, including their sensitivity and susceptibility to being traumatized by ammonia, moisture, temperature changes, plant power failures, and other changes in operating conditions. Also, conventional Ni-mordenite catalysts suffer from the disadvantage of requiring up to three or more days to get lined out during reactor setup, during which period of startup, there is no significant acceptable production across the catalyst. The present invention provides a TDP process utilizing a Ni-mordenite catalyst that overcomes these deficiencies while allowing the production rates to be increased several fold and the selectivities to be improved at the same time.

SUMMARY OF THE INVENTION

In accordance with the present invention, there is provided a process for the disproportionation of a substantially pure toluene feedstock over a dealuminated nickel-mordenite catalyst wherein increased production rates of up to three times normal commercial rates can be achieved without detrimental effect on the product stream, catalyst activation, or catalyst life.

BRIEF DESCRIPTION OF THE DRAWING

FIG. 13 is a graph of the deactivation rate of the catalyst from FIG. 12.

FIGS. 14 and 15 illustrate the product selectivities for the second catalyst when run at double space velocity.

DESCRIPTION OF THE PREFERRED EMBODIMENTS

Figure 1:
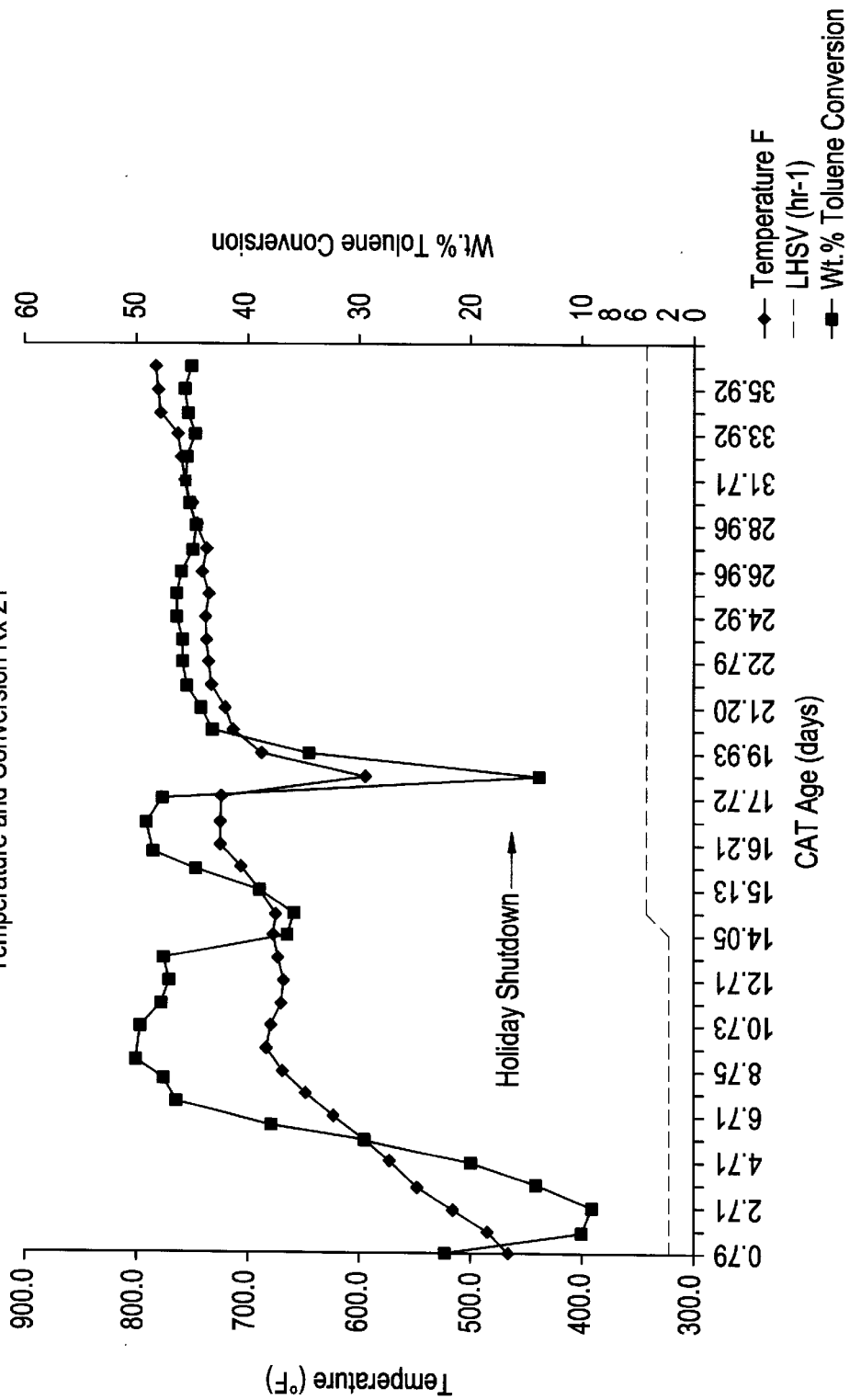
FIG. 1 is a graph illustrating toluene conversion in a disproportionation process carried out over a nickel modified mordenite catalyst illustrating temperature and conversion rates, over time.

As evident in the patents previously discussed, the use of nickel modified catalysts in toluene disproportionation is well known in the art. The present invention, however, provides an improved mode of conducting toluene disproportionation over a nickel modified mordenite catalyst wherein the catalyst has been selected to allow manyfold increases in the production rates without loss of catalyst activity or selectivity.

In accordance with the invention, there is provided a toluene disproportionation process employing a catalyst of the mordenite type modified by the inclusion of a metallic hydrogenation component, more specifically nickel. The mordenite catalyst employed in the present invention preferably exhibits a silica-to-alumina mole ratio of between about 5 and about 50, and more preferably about 20. One particularly advantageous Ni-Mordenite catalyst that was found to be useful in the present invention was that, commercial catalyst designated as CN-4091, manufactured and sold by UOP, 25 East Algonquin Road, Des Plaines, Ill. 60017. This catalyst exhibits the following typical physical and chemical properties: form-extrusion; diameter 1.6 to 1.8 mm; compacted bulk density of 37+/−4 lbs/ft$^3$; crush strength (average of 15 pellets) of about 8 lbs.; Hg Pore Volume of>0.3 cc/g; BET Surface Area of >300 m$^2$/g; and % LOI (Loss of Ignition) at 1000° F. of 4% max.

The mordenite disproportionation catalyst employed in the present invention has been modified by the inclusion of nickel. Applicant's experimentation suggests that best results are obtained by utilizing a catalyst made up of no less than about ½ percent weight percent nickel. It is known that low nickel content mordenite catalysts provide toluene conversion and selectivity to xylenes and benzene but exhibit poor aging qualities. Experimentation has determined that, while greater amounts of nickel can be used without added benefit, a practical upper limit of nickel content in the catalyst is about 1.5 weight percent.

The present invention resulted from studies conducted over a period of approximately 100 days utilizing a laboratory reactor. In the presence of hydrogen gas, a substantially pure toluene feedstock was disproportionated over a nickel modified mordenite catalyst under the following initial conditions: temperature 680–800° F.; mordenite silica-to-alumina molar ratio catalyst of about 20; hydrogen/toluene mole ratio of about 1 up to about 4; feedstock liquid hourly space velocity (LHSV) between 2.0–6.0; and at an inlet pressure of about 600 psig.

The present process was devised in a laboratory reactor. Utilizing a conventional catalyst, the commercial space velocity of the TDP reaction was previously believed to be limited to about 2 $hr^{-1}$. The laboratory reactor was set up to simulate the same reaction obtained in the commercial reactor by inserting in the laboratory reactor the above described commercially available nickel mordenite catalyst which was designated as CN-4091, it was found that the production rate of the reactor could be increased several-fold without adversely affecting the catalyst life, the selectivity, or the activity. During the first run through the reactor, a set of base conditions were established that corresponded to conventional commercial conditions. Those conditions were LHSV=2.0 $hr^{-1}$;

Pressure=600 psig (inlet);

Temperature=adjusted to obtain 47% toluene conversion;

Hydrogen rate relative to hydrocarbon=initial 1:1 (molar ratio);

Subsequent H:HC=4:1 (molar ratio).

After the initial base conditions were established in the laboratory reactor, the space velocity of the toluene feed/hydrogen was doubled providing an increase in throughput of 100% over the base case. Two test runs were performed, the first being at a hydrogen:hydrocarbon ratio of 2.3:1. It was initially intended that the H:HC ratio be established at 4:1, however, equipment available did not allow the H:HC ratio to be maintained at a level higher than 2.3:1. However, with an equipment change another test was conducted wherein the H:HC molar ratio was maintained at the desired level, i.e., 4:1.

In TDP process runs using commercial reactors, the general conditions of operation at the start of run require a temperature of around 660° F. to 670° F. which is necessary to reach a 47% toluene conversion. With the conventional process a deactivation rate of around 1.2° F. per day is observed based on the volume of feedstock pumped across the catalyst, however, the deactivation rate can be calculated at 5.5° F./barrel/pound catalyst. Utilizing the volume deactivation rate rather than the time deactivation rate, one can compare the commercial process with the process of the present invention on an equal basis.

FIG. 1 is a graphic illustration of the present process wherein the feed material was introduced into the laboratory reactor at a space velocity of 2 $hr^{-1}$. The desired toluene conversion rate was obtained at approximately 11 days into the run. At this point, the H:HC ratio was 4:1. After 3 days the space velocity through the reactor was doubled to 4 $hr^{-1}$. The hydrogen rate was increased to the maximum capacity of the equipment resulting in an H:HC ratio of 2.3:1. A loss in conversion was observed of approximately 10%. To offset this loss in conversion, the temperature of the reactor was increased approximately 50–55° F. to bring the conversion level back to a desired figure of 46–47%.

It should be noted in FIG. 1 that a large dip in the temperature and conversion rate is indicated at approximately 18 days into the run. This was due to a shutdown of the equipment for a holiday period, however, after the shutdown the reactor was started up again and the catalyst exhibited almost exactly the same activity, reaching desired conversion levels with just a few degrees hotter reaction temperature. This experimental run continued for another 2 ½ weeks during which time the temperature was increased to maintain the conversion at approximately 46%.

Figure 2:
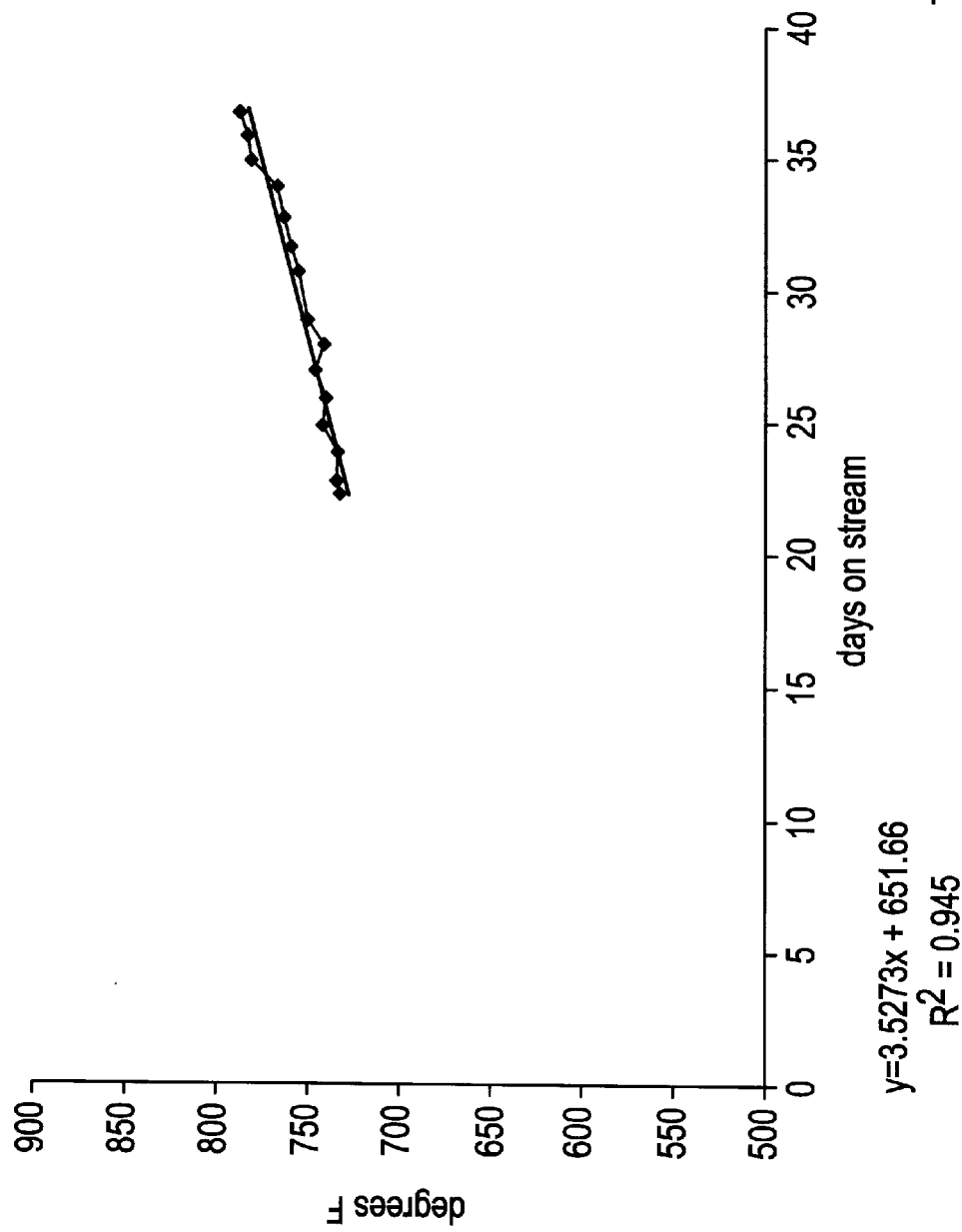
FIG. 2 is a graph of the toluene disproportionation process displaying catalyst deactivation rate, over time.
Figure 3:
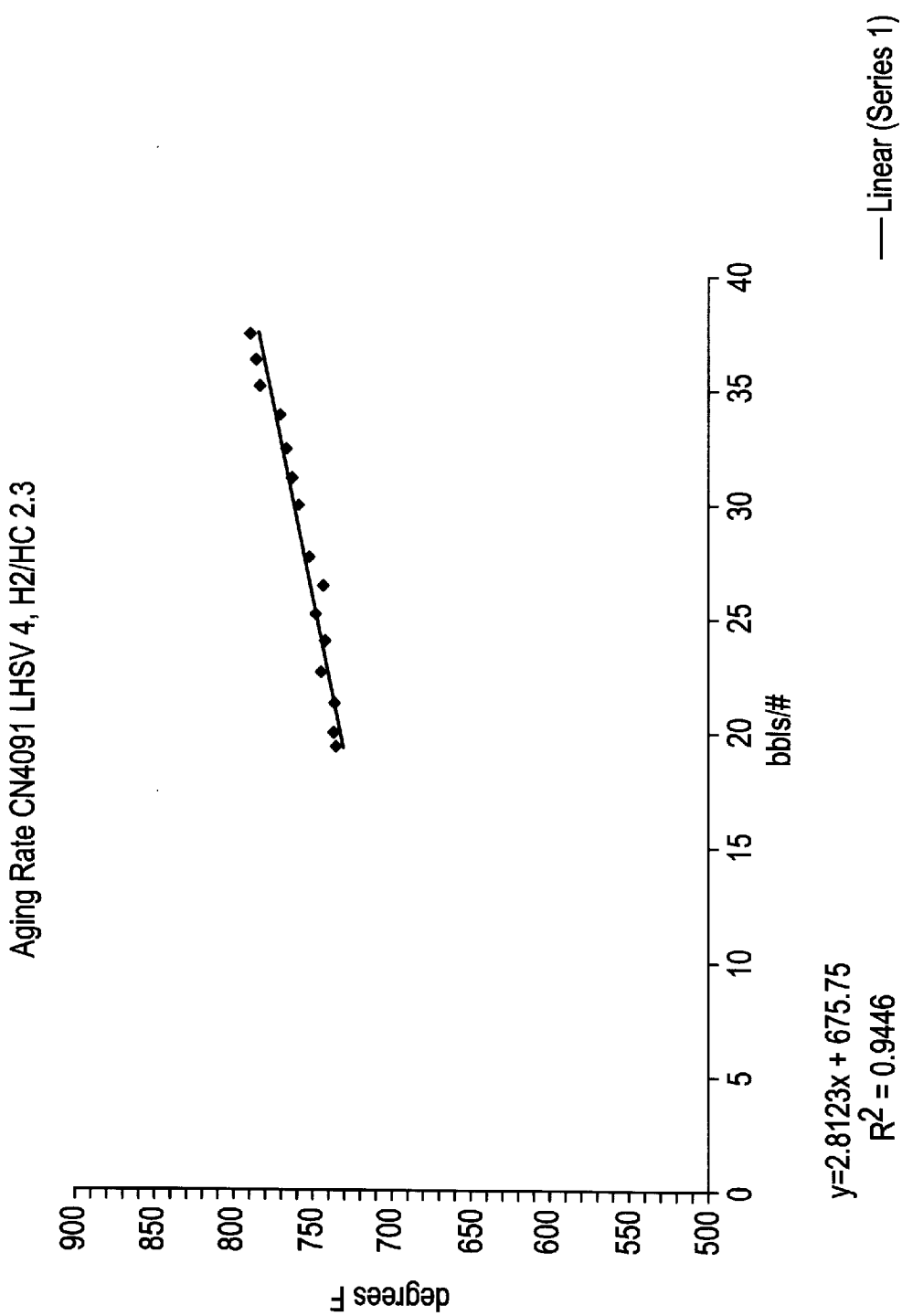
FIG. 3 is a graph illustrating the process catalyst aging rate on a volume basis.

FIG. 2 is a graphic representation of the daily deactivation rate of the catalyst. FIG. 2 indicates that a daily increase of 3.5° F. in the reactor was needed to maintain the 46–47% conversion level. This, as expected, was greater than the conventional requirement of 1.2° F./day of the base case as previously established in commercial runs and in the base run. However, when calculated on a volume basis rather than a time basis, as graphically indicated in FIG. 3, the requirement dropped to 2.8° F. per barrel per pound of catalyst. This compares favorably to the base case of 5.5° F. per barrel per pound of catalyst in the conventional run. The increased improvement is substantially significant and higher than the tolerance or inherent error in the testing procedure.

Figure 4:
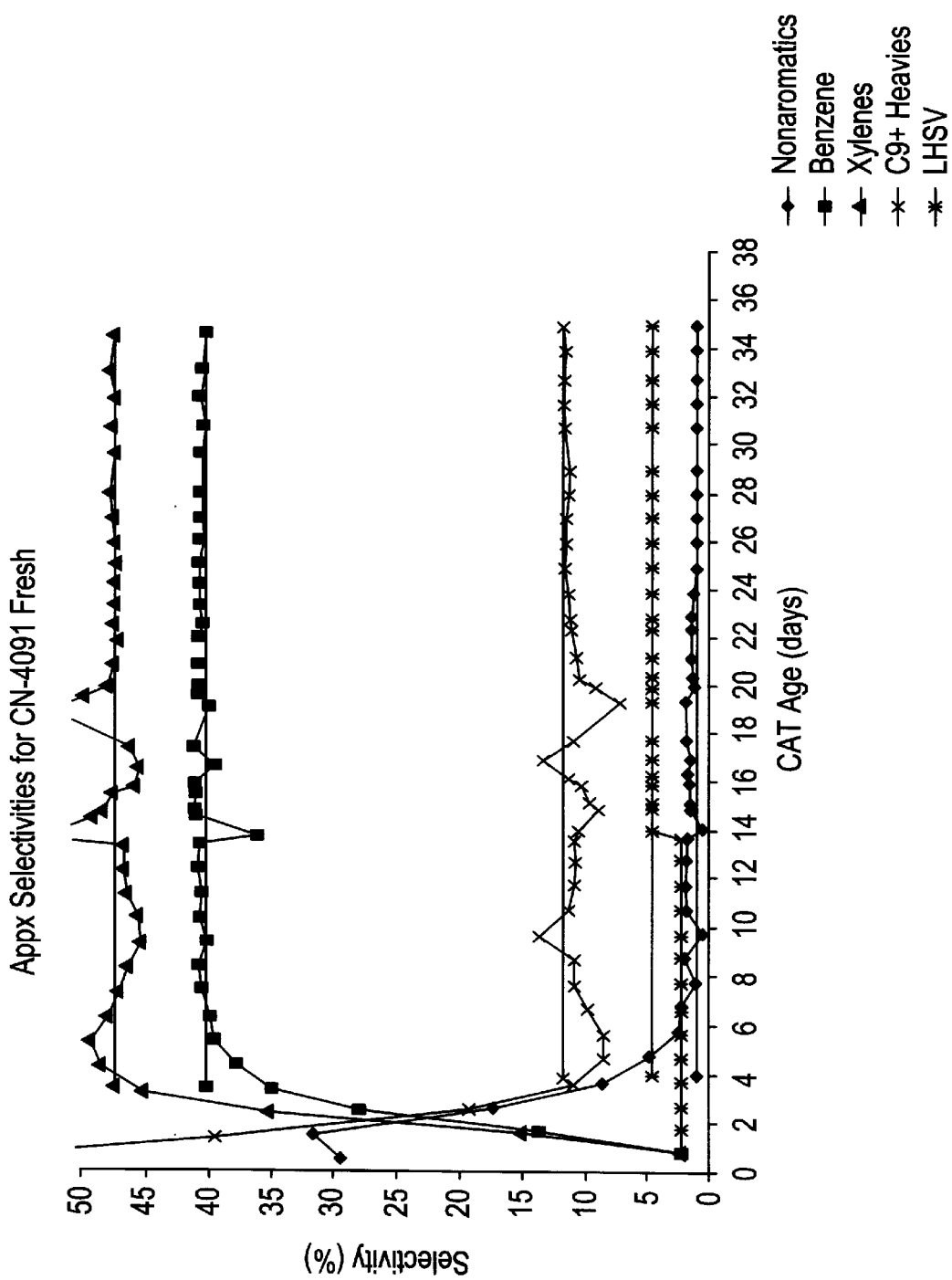
FIG. 4 illustrates the product selectivities for the TDP process.

FIG. 4 indicates graphically the selectivities obtained during the higher space velocity test. As stated previously, the space velocity was doubled on day 14. Just prior to the increase in space velocity the reactor had reached a 47% conversion at the conventional space velocity of 2 $hr^{-1}$. FIG. 4 illustrates that there was no dramatic change in selectivity with the doubling in the space velocity. In fact, the production of "heavies" increased by about 1% which was offset by a decrease in the nonaromatics production.

Figure 5:
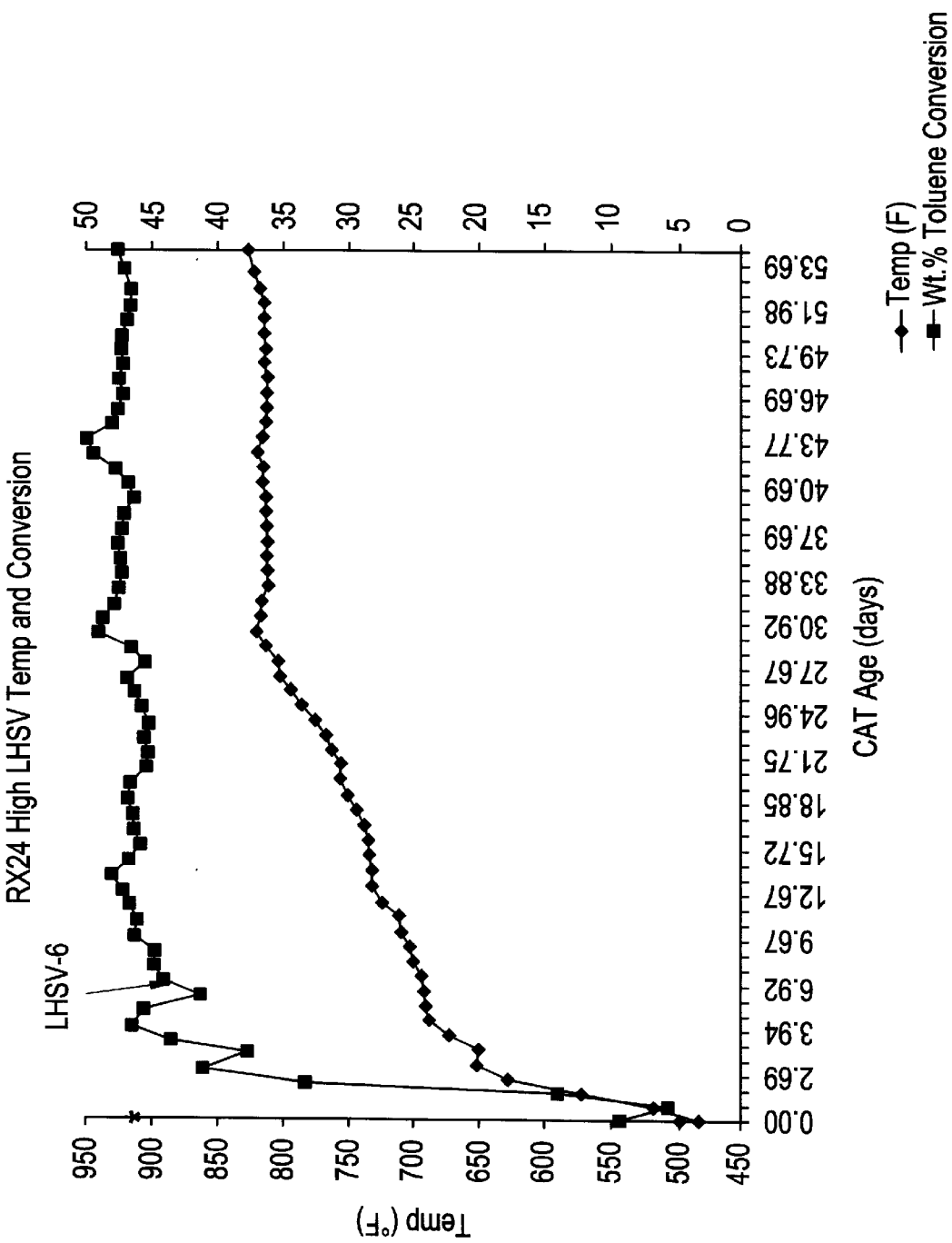
FIG. 5 is a graph comparing temperature and conversion rates to time on stream.

FIG. 5 shows a graphic illustration of a new run after a change in the equipment allowed the H:HC ratio to be adjusted to 4:1. In FIG. 5 the process is graphically illustrated with conversion and temperature versus time. The start of run temperature required to reach the desired 47% conversion level was about 40° F. above the base case. One notable feature of this graphic illustration in FIG. 5 is the plateau in temperature which occurred after day 30. The plateau temperature of 810° F. was within experimental error of that which was measured in previous work at the conventional space velocity of 2 $hr^{-1}$. It should also be noted from the figure that at approximately day 6.9 the space velocity was tripled over the conventional rate to a figure of 6 $hr^{-1}$. The effect of this was much more beneficial than expected. For example, the loss in conversion of only 5–6% was noted. One skilled in the art would normally have expected a loss of conversion of at least 10% from a tripling of the space velocity from 2 $hr^{-1}$ to 6 $hr^{-1}$. This change indicates that it may be possible to increase the flow rates even higher than the 6 $hr^{-1}$ indicated on the graphic illustration in FIG. 5.

Thus, it has been graphically and experimentally shown by the description above given with respect to FIGS. 1–5 that with the catalyst described herein there is no dramatic negative effect on the catalyst when activity is measured on the volumetric basis and the throughput rates are increased twofold to threefold over conventional rates. In addition, when the space velocity was doubled, a temperature increase of 40–50° F. was required to maintain conversion at the desirable level of 47%. It was also found that xylene isomer selectivity did not change significantly with increased throughputs. Also, doubling the space velocity did not increase the deactivation rate at the start of run when measured on a volumetric basis. One part of the experiment indicated that space velocities as high as 6 $hr^{-1}$ or even higher could be utilized without negative or detrimental effects on the catalyst. Furthermore, the catalyst activity stabilized at approximately 810° F. at the double throughput which is roughly the same temperature as conventional studies run at conventional throughputs.

FIGS. 6–15 illustrate a second embodiment of the inventive process in which a second catalyst was utilized instead of the catalyst of FIGS. 1–5. In the second embodiment, a toluene disproportionation process was carried out employing a second catalyst of the mordenite type which also was modified by the inclusion of a metallic hydrogenation component, nickel. The mordenite catalyst employed in the second embodiment exhibited a silica-to-alumina mole ratio of between about 10 and about 50, and more preferably about 20. The catalyst used was a commercial catalyst designated as T-2581 which is manufactured and sold by United Catalyst, Inc., 1227 South 12th Street, Louisville, Ky. 40210. This catalyst exhibits the following typical physical and chemical properties: form-extrusion; size 1.4 to 1.6 mm; compacted bulk density of 37+/−3 lbs/ft$^3$; a crush strength for a 15 pellet average of about 1.1+/−0.2 lbs/mm; Hg Pore Volume greater than 0.3 cc/g; BET Surface Area exceeding 200 m$^2$/g; and a percent LOI at 1000° F. of less than 8.

As with the previous catalyst in the first embodiment, the disproportionation catalyst employed in the second embodiment has also been modified by the inclusion of nickel. Experimentation suggests that the best results are obtained by utilizing a catalyst made up of no less than 0.3 weight percent nickel, and preferably in the range of approximately 0.9 percent. While greater amounts of nickel can be used without added benefit, a practical upward limit of nickel content in this catalyst is about 1.5 weight percent.

In the second embodiment, studies were conducted over a period of approximately 100 days utilizing the same type laboratory reactor as in the first embodiment. In the presence of hydrogen gas, a substantially pure toluene feedstock was disproportionated over a nickel-modified mordenite catalyst under temperature conditions of 680–800° F.; a mordenite silica-to-alumina molar ratio of about 20; a hydrogen/toluene mole ratio of about 1 up to about 4; a feedstock liquid hourly space velocity (LHSV) between 2.0 and 6.0; and an inlet pressure of about 600 psig. Utilizing the commercial catalyst designated T-2581 it was found that as in the first embodiment the production rate of the reactor could be increased several-fold without adversely affecting catalyst life, the selectivity or the activity. During the first run through the reactor a set of base conditions were established that corresponded to conventional commercial operation. These conditions were:

LHSV=2.0 per hour
Pressure=600 psig (inlet);
Temperature=adjusted to obtain approximately 47% toluene conversion;
Hydrogen rate relative to hydrocarbon=initial 1:1 (molar ratio); and subsequent 4:1 (molar ratio).

Figure 6:
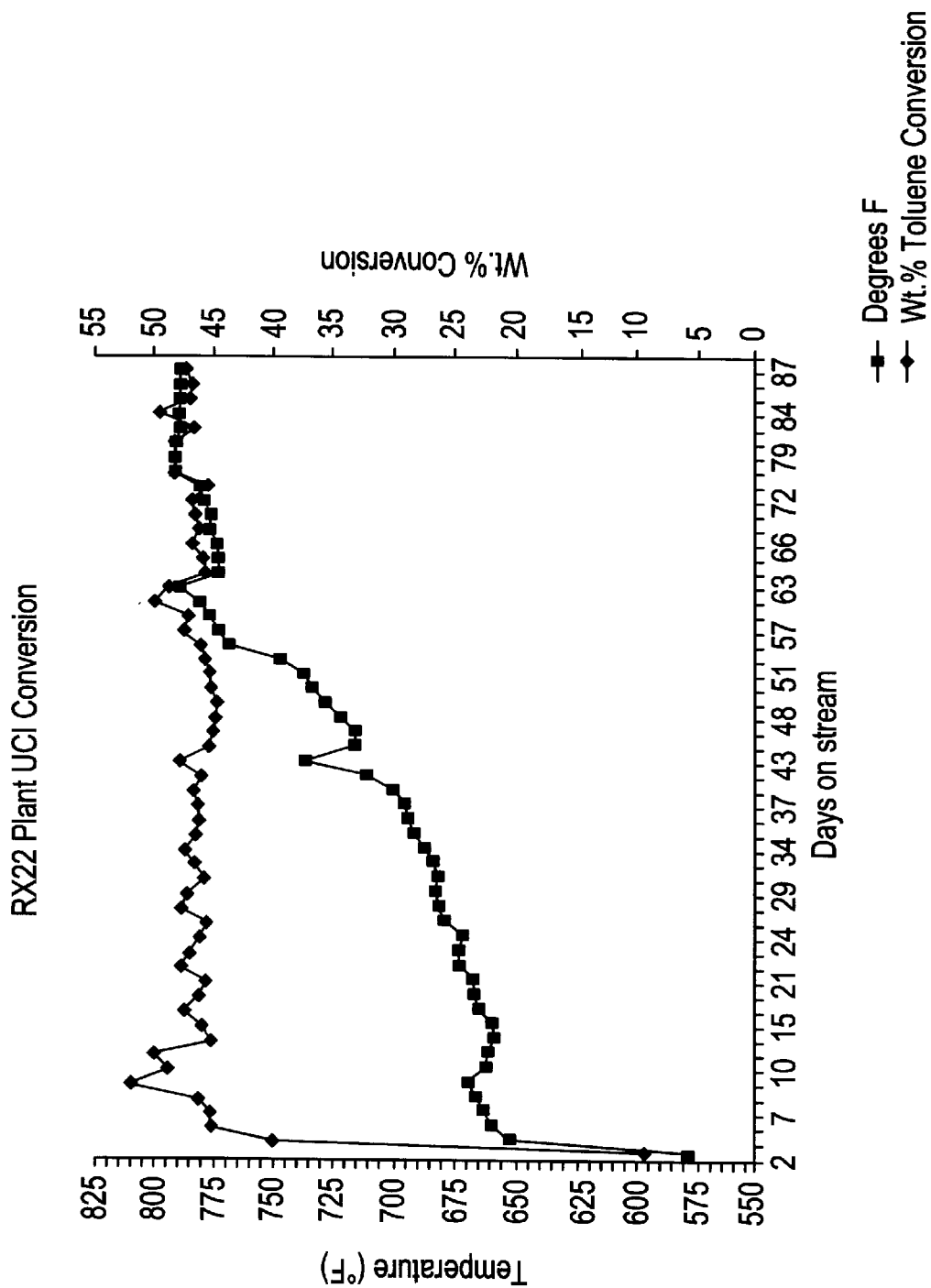
FIG. 6 is a graphical representation of the relationship between reactor temperature and toluene conversion over time for a different catalyst from that disclosed in the previous FIGS. 1–5.

After the initial base conditions were established in the laboratory reactor, the space velocity of the toluene feed/hydrogen was doubled, providing an increase throughput of 100% over the base case. The temperature was adjusted to maintain the toluene conversion level at 47%. The hydrogen rate relative to the hydrocarbon was initially set at 1:1 (molar ratio) and subsequently raised to 2:1 (molar ratio). The change in space velocity in the lab reactor relative to the above noted base case corresponds to a similar increase in commercial feed rate. Referring to FIG. 6, there is illustrated a graph of reactor temperature and toluene conversion versus time on stream. A temperature of 660–670° F. was needed to reach a 47% toluene conversion at the start of the run. A daily temperature increase was required to maintain the conversion until a final plateau temperature of about 785–790° F. was reached. In order to compare the start of run deactivation rate of the base case against deactivation rate at different feed rates, it is necessary to express the rates on the same basis for all experiments. Thus, deactivation rates are reported relative to the total liquid flow over the catalyst expressed as barrels of feed per pound of catalyst (bbl/lb).

Figure 7:
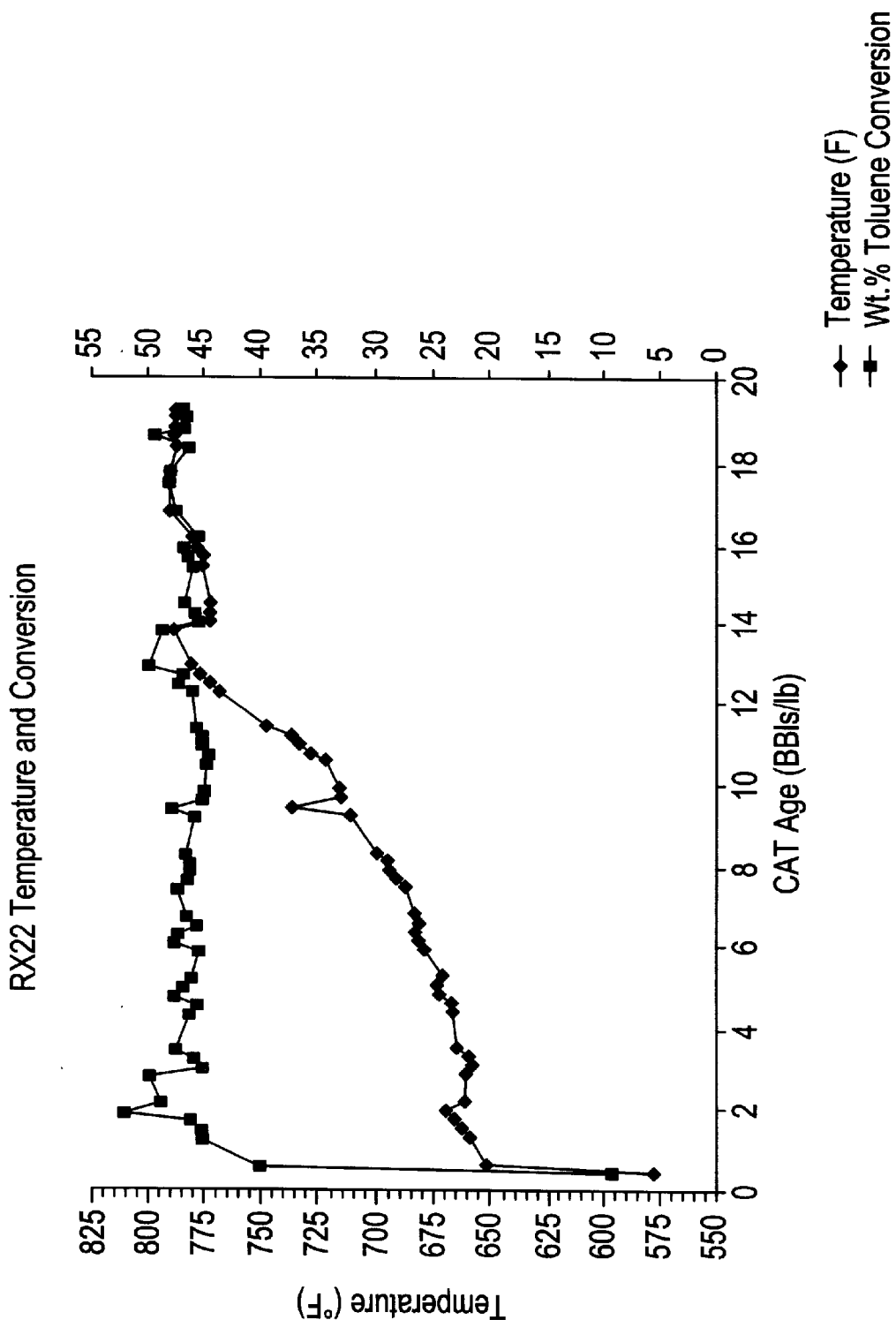
FIG. 7 is a graphical representation of the reaction temperature and toluene conversion relative to the cumulative volume of feed pumped across the catalyst of FIG. 6.
Figure 8:
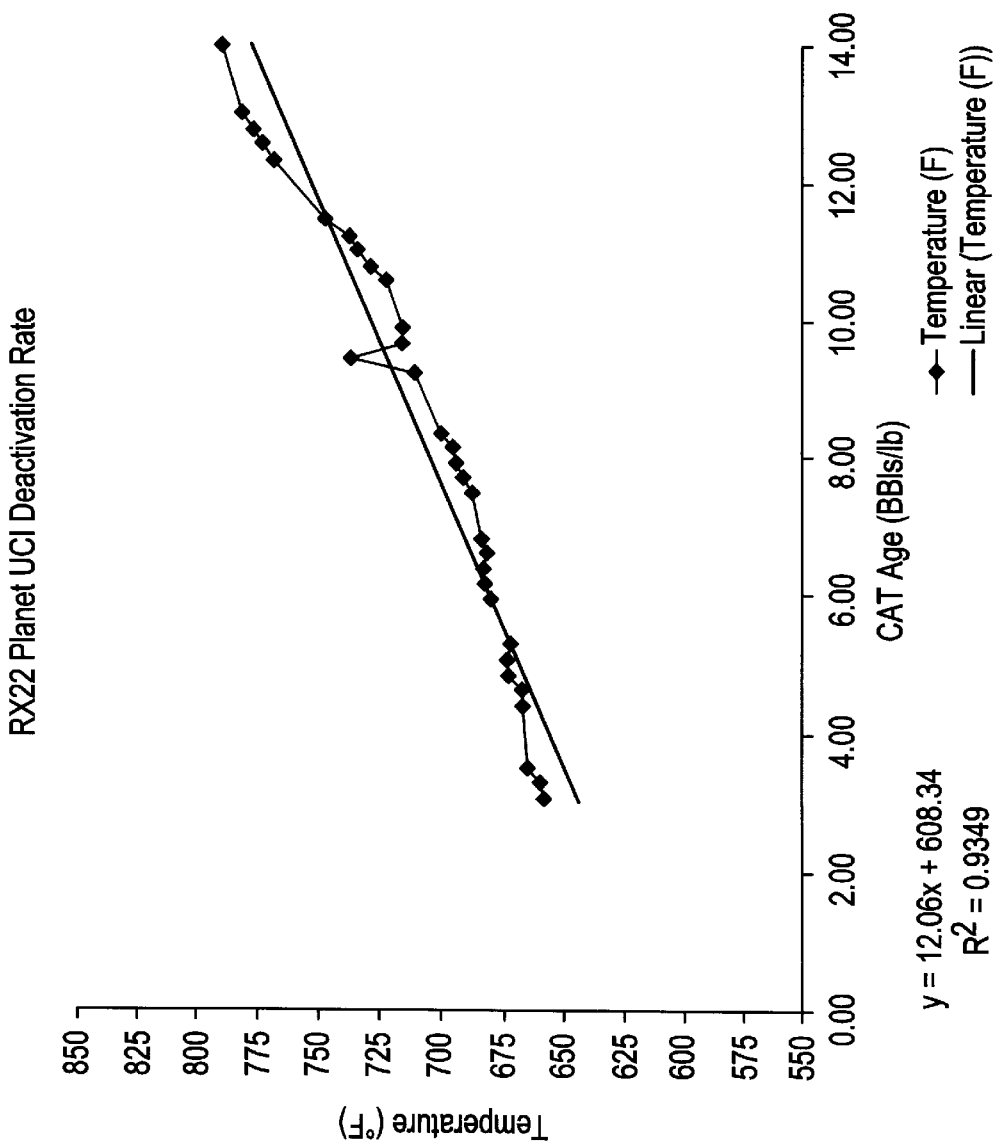
FIG. 8 represents a graphical illustration of the catalyst deactivation rate in degrees temperature versus cumulative volume for the catalyst of FIG. 6.

FIG. 7 indicates the reactor temperature and toluene conversion relative to the cumulative volume of feed pumped across the catalyst. This Figure shows that the initial deactivation at the start of the run was non-linear to a certain extent. Likely the cause was that the temperature increases applied between 8 and 10 pounds per barrel were not sufficient to maintain the desired conversion level of 47%. This may have resulted in a greater increase in temperature for the subsequent adjustments in order for the conversion to catch up. However, a linear approximation gives an average deactivation rate for the initial part of the run. For the base case test, the average deactivation rate was 12.06° F. per pound of catalyst as indicated in FIG. 8.

Figure 9:
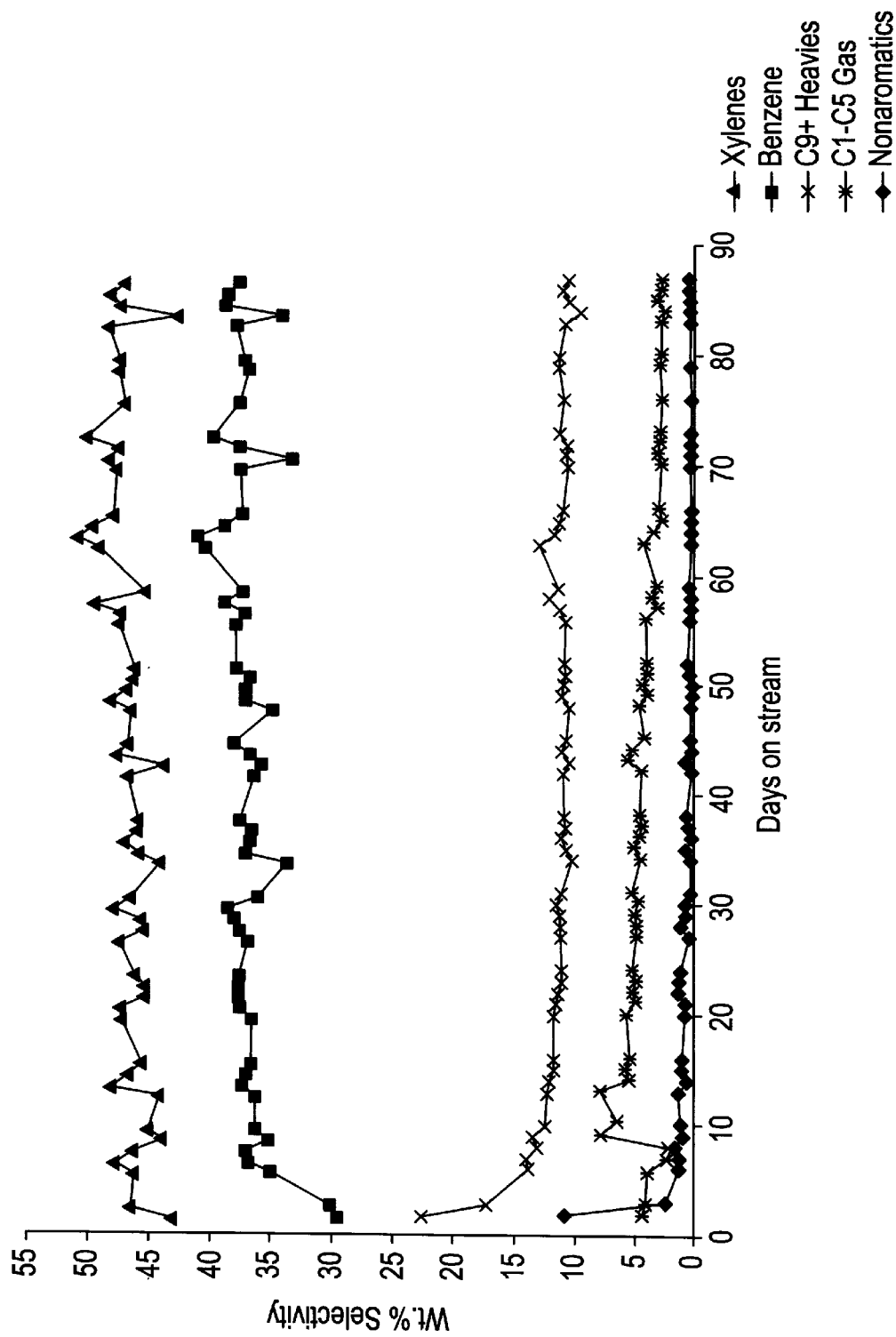
FIGS. 9 and 10 illustrate the product selectivities relative to the days on stream and the barrels per pound of catalyst.
Figure 10:
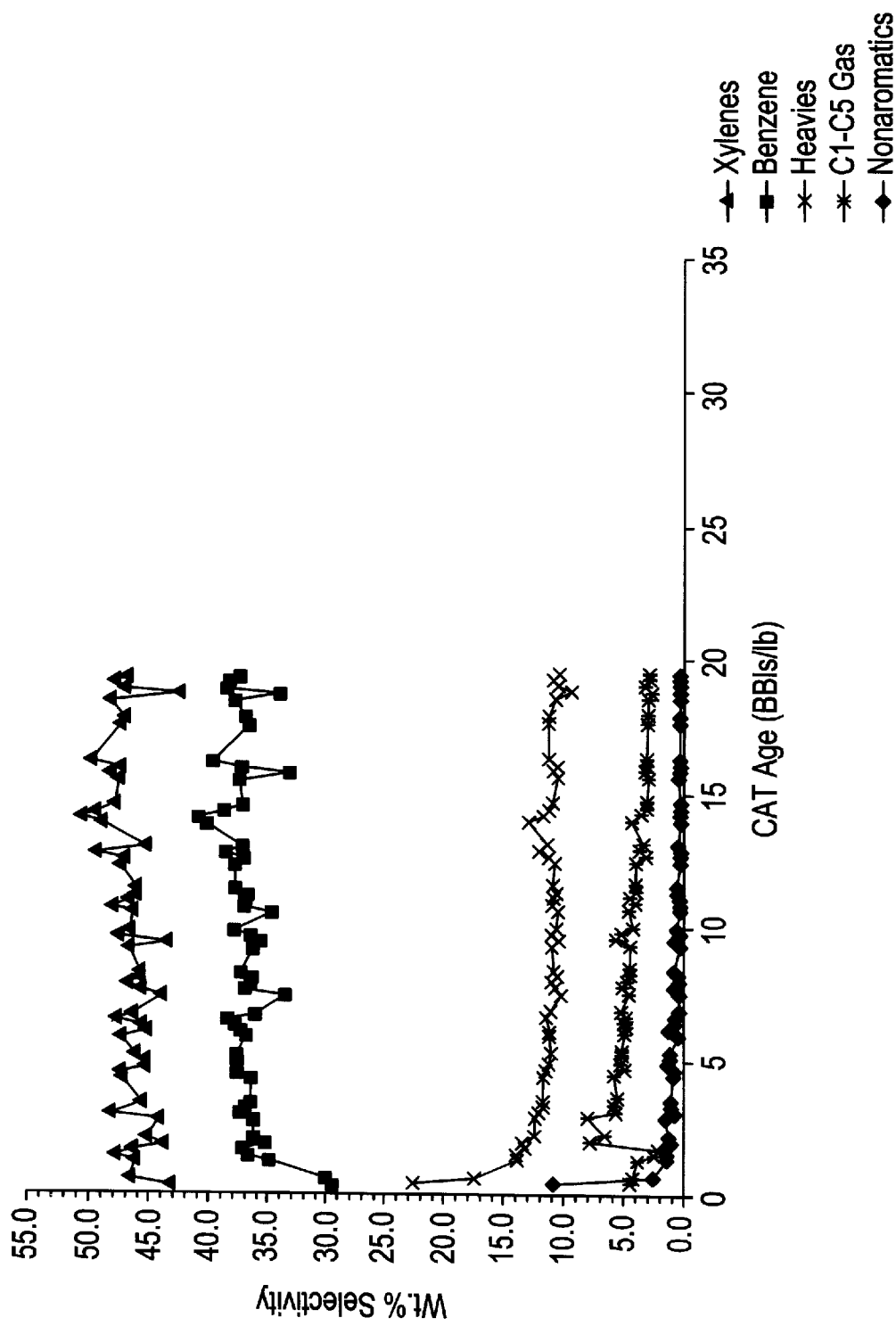
Figure 11:
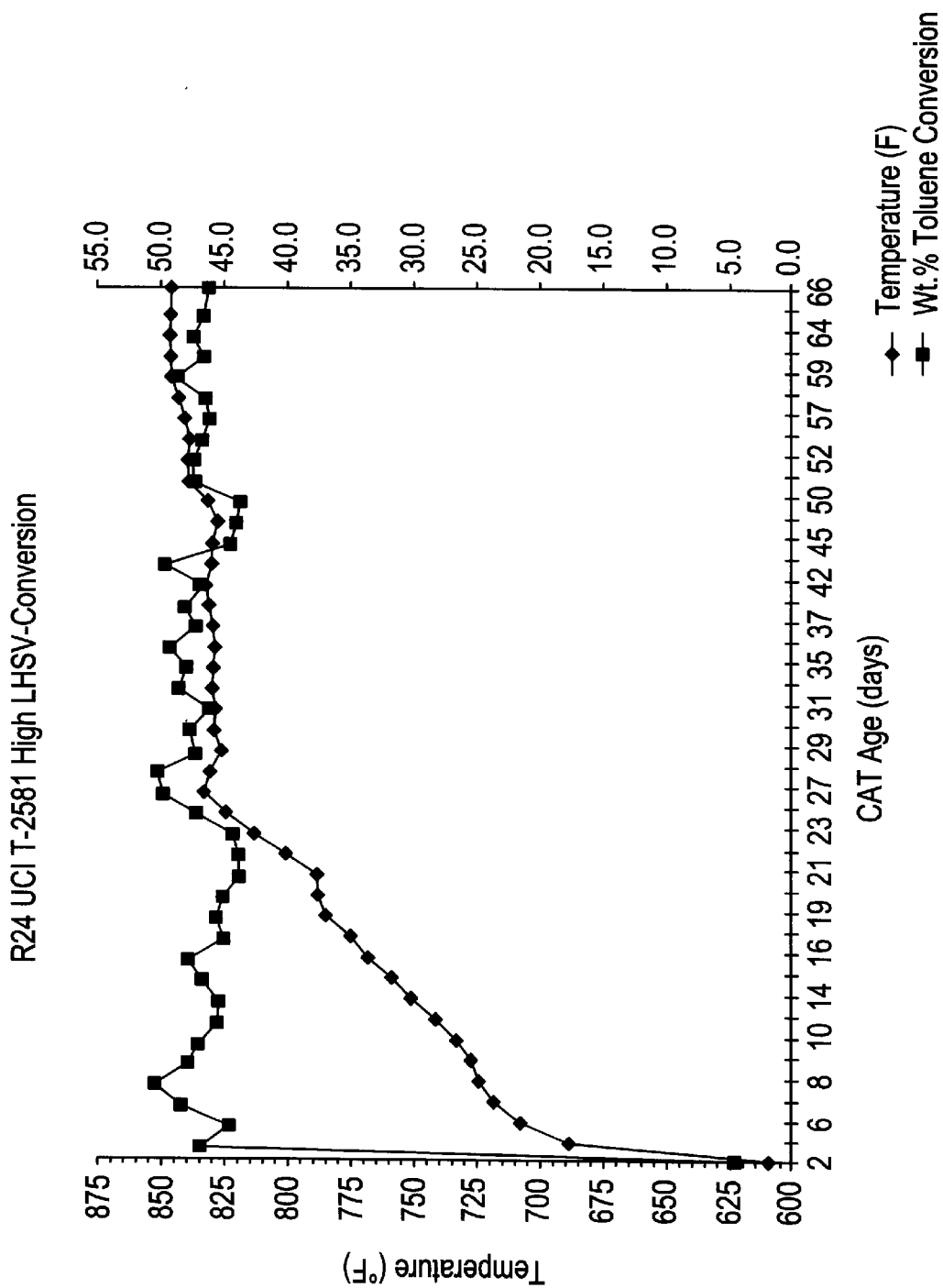
FIG. 11 is a plot of the catalyst of FIG. 6 relating space velocities and conversions versus temperature and catalyst age.

After the initial deactivation, the base case catalyst reached a plateau temperature of 785–790° F. after pumping 14 barrel/pound. FIGS. 9 and 10 show the product selectivities relative to days on stream and barrels per pound respectively. The selectivity of the second embodiment catalyst ranged from approximately 47% for xylene, 38% for benzene, 11% for heavies, 2% for gases, and down to less than 1% for nonaromatics. The increase in gas production early in the run was probably the result of the increase in hydrogen to hydrocarbon ratio which is a part of the customary start up procedure. FIG. 10 is a chart of the selectivities plotted versus the catalyst age in barrels per pound. The selectivities there improve until leveling out at approximately 5 barrels per pound, with the same selectivities mentioned above with respect to FIG. 9. FIG. 11 is a plot of the second catalyst which has been run at double the normal space velocity. The initial conversion of 47% was reached on day 3. However, the faster daily deactivation rates quickly necessitated that the reactor be run at increasingly higher temperatures. A plateau temperature was reached at approximately 830° F. which is roughly 40° F. higher than the base case. The loss in conversion on day 45, which resulted in a temperature increase on day 50, was due to a loss of toluene feedstock. With a reactor temperature of 830° F. there was probably enough heat to alter the state of the nickel in the catalyst by either increasing the extent of reduction, or by promoting agglomeration, or both. Although the process stabilized at higher temperature, this ultimately lead to reactor shutdown. The temperature was slightly under 850° F. which is the normal end- of-run temperature for a commercial unit.

Figure 12:
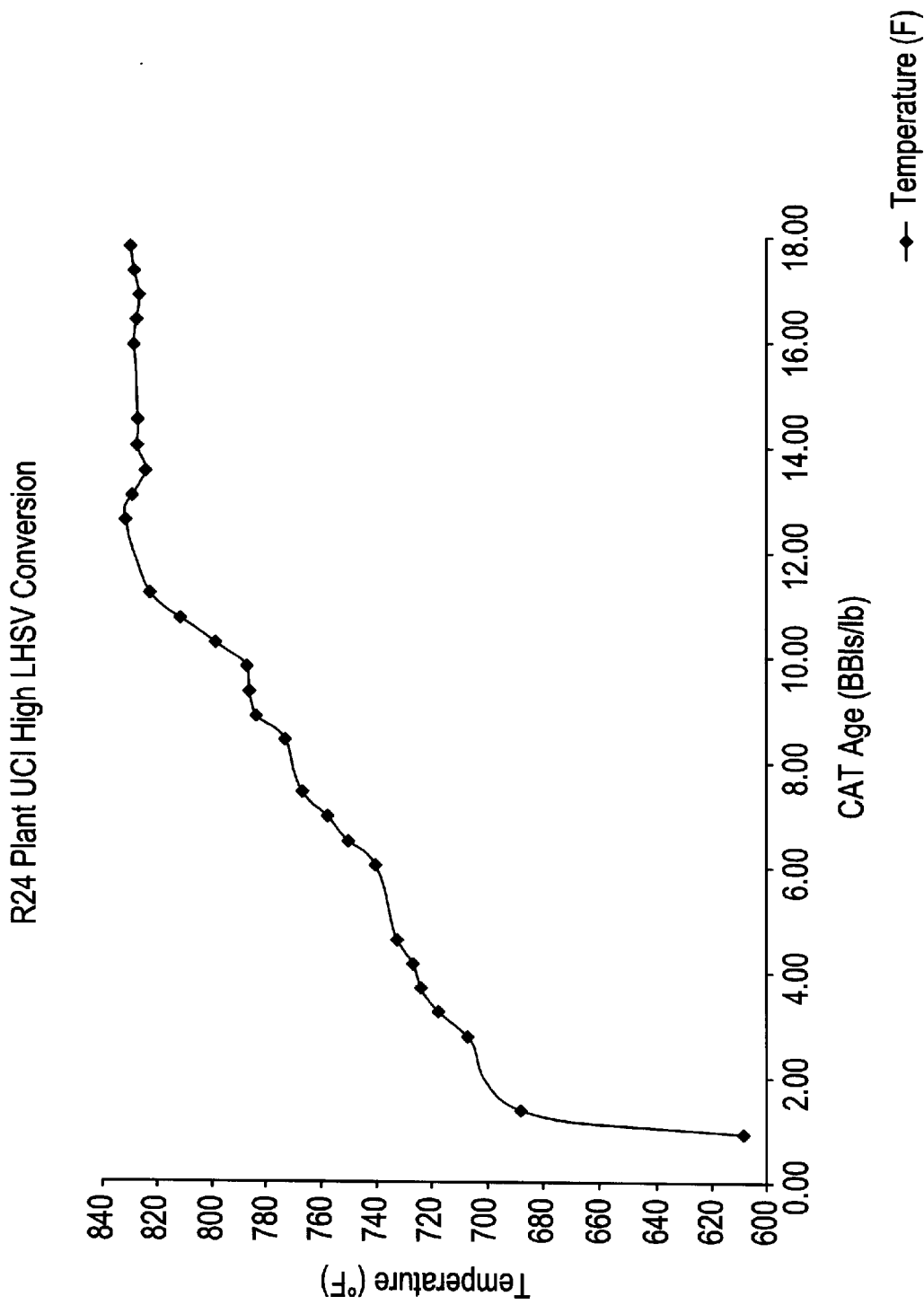
FIG. 12 is a plot of reactor temperature versus barrels per pound of catalyst at increased space velocities for the catalyst of FIG. 6.

FIG. 12 is a plot of the reactor temperature versus barrels of feedstock per pound of catalyst. Utilizing these units of measurement allows the analyst to make a direct comparison with the base case. A plateau temperature was reached at about 13 barrels of feed per pound of catalyst, which is within experimental tolerances of the 13–14 barrels per pound measured for the base case.

FIG. 13 is a detail of the deactivation rate from FIG. 12. A linear regression shows that the catalyst deactivated at a rate of 12.5° F. per barrel of feed per pound of catalyst. This was almost equivalent to the value measured for the base case of 12.06° F./barrel/pound as shown in FIG. 8. Consistent with the first embodiment, the increased space velocity did not affect the rate at which the catalyst aged relative to the cumulative flow of feedstock over the catalyst. FIGS. 14 and 15 show the product selectivities for the second embodiment catalyst when run at double space velocity, or 4 per hour. These Figures show the selectivity relative to time and relative to cumulative feed flow over the catalyst, respectively. Comparison of FIGS. 9 and 14, both relative to time, shows that the product selectivities stabilized or lined out quicker for the high space velocity run than for the conventional run (base case). For example, for the high space velocity test, the make of heavies, gas, and nonaromatic production all dropped faster and to lower values than did the base case. When compared on a barrel of feedstock per pound of catalyst basis, these trends are not nearly as clear however. But, the high space velocity cases did retain advantages in selectivity initially. Total xylene selectivities were comparable but there was a 1–2% advantage in benzene selectivity for the high space velocity case. As stated earlier above, this was probably due to production of less undesirable byproducts from the high space velocity test, however, as the run progressed and the temperature was increased, the selectivities for the high space velocity test approached those of the base case. At the time each run was terminated the selectivities were almost identical.

Thus, the present invention indicates that initial deactivation rates of conventional catalyst disproportionation processes and for double space velocity processes run at half the H:HC ratio are the same within tolerances of the test when reported on a barrel of feedstock per pound basis. Also, the plateau temperature for the runs utilizing double space velocity was approximately 40° F. higher than the base case, but once the plateau temperature was reached, no additional temperature increases were required to maintain selectivity. The double space velocity runs provided 2% higher benzene product selectivity than the conventional base case runs. For both catalysts in the embodiments 1 and 2 above, a plateau temperature was reached at about 13 barrels of feedstock per pound of catalyst. Thus, the present invention describes processes utilizing nickel mordenite catalysts for doubling the throughput of toluene disproportionation reactors, without degrading or seriously decreasing the selectivities, activities, or catalyst life, when based on a throughput per pound of catalyst rate rather than on a straight time lapsed basis.

While the invention has been described with reference to particular embodiments thereof, it will be apparent to those skilled in the art that various changes and modifications can be made without departing from the spirit of the invention or from the scope of the appended claims.

What is claimed is:

1. A process for disproportionation of toluene to benzene and xylene, wherein a toluene/hydrogen feedstock is passed over a nickel-mordenite catalyst at a reaction temperature sufficient to provide toluene conversion to xylene at a rate of about 46 to 47 percent, the improvement comprising selecting a catalyst of dealuminated nickel-mordenite structure having a silica-to-aluminum mole ratio of between about 10 and about 50, and extruded form having a size of about 1.4 mm to about 1.6 mm, a compacted bulk density of about 37+/−lbs/ft$^{-1}$, 15 pellet average crush strength of about 1.1+/−0.2 lbs, an Hg pore volume greater than about 0.3 cc/g, a BET surface area exceeding about 200 m$^2$/g, and a percent LOI at 1000° F. of less than about 8, wherein the liquid hourly space velocity of said toluene feedstock over said catalyst is thereafter doubled, from about 2 hr$^{-1}$ to about 4 hr$^{-1}$ and the temperature of the reaction is raised a sufficient amount to maintain toluene conversion at about 46 to 47%.

2. The process of claim 1 wherein said temperature is maintained continuously at said 47 percent conversion level.

3. A method of forming benzene and xylenes from a toluene feedstock comprising flowing said feedstock across a bed of nickel-mordenite catalyst in the presence of hydrogen at a temperature sufficient to produce a predetermined desirable conversion rate of the feedstock into xylenes at a liquid hourly space velocity of about 2 hr$^{-1}$; thereafter increasing the liquid hourly space velocity of the feedstock to about 4 hr$^-$and simultaneously increasing the hydrogen feed in amounts sufficient to maintain about the same molar ratio of hydrogen to hydrocarbons as initially present in the toluene/hydrogen feed, and additionally simultaneously increasing the temperature of the reaction sufficiently to maintain said predetermined desirable conversion rate.

4. The method of claim 3 wherein said H:HC molar ratio is about 4:1 and said predetermined conversion rate is about 46 to 47 percent.

5. The method of claim 4 wherein said liquid hourly space velocity is increased to about 6 hr$^{-1}$.

6. The method of claim 4 wherein said reaction temperature is initially about 680° F. and is eventually raised to about 810° F.

7. The method of claim 5 wherein said reaction temperature is eventually raised to about 810° F.

* * * * *